US 7,373,847 B2

(12) United States Patent
Cole

(10) Patent No.: US 7,373,847 B2
(45) Date of Patent: May 20, 2008

(54) AUTOMATIC THERMAL DESORPTION APPARATUS AND METHOD

(75) Inventor: Alun Cole, Glyn Ogwr (GB)

(73) Assignee: Markes International Limited (GB)

( * ) Notice: Subject to any disclaimer, the term of this patent is extended or adjusted under 35 U.S.C. 154(b) by 115 days.

(21) Appl. No.: 10/536,663

(22) PCT Filed: Dec. 1, 2003

(86) PCT No.: PCT/GB03/05242

§ 371 (c)(1),
(2), (4) Date: Dec. 8, 2005

(87) PCT Pub. No.: WO2004/051227

PCT Pub. Date: Jun. 17, 2004

(65) Prior Publication Data

US 2007/0163326 A1    Jul. 19, 2007

(30) Foreign Application Priority Data

Nov. 30, 2002  (GB) .................................. 0228006.3

(51) Int. Cl.
*G01N 1/20* (2006.01)
(52) U.S. Cl. ................................. 73/863.01
(58) Field of Classification Search ............. 73/863.01, 73/864.81, 964.83; 436/43
See application file for complete search history.

(56) References Cited

U.S. PATENT DOCUMENTS

| 4,701,306 A | 10/1987 | Lawrence et al. ........... 422/101 |
| 5,014,541 A | 5/1991 | Sides et al. ................. 73/23.41 |
| 5,402,668 A | 4/1995 | Murakami et al. .......... 73/19.02 |
| 6,167,767 B1* | 1/2001 | Mengel et al. ............. 73/863.21 |
| 6,192,766 B1 | 2/2001 | Gårdhagen et al. ........ 73/863.12 |
| 6,223,584 B1 | 5/2001 | Mustacich et al. .......... 73/23.41 |
| 6,409,968 B1 | 6/2002 | Takahashi ..................... 422/64 |
| 2002/0157483 A1 | 10/2002 | Lo et al. .................... 73/864.71 |
| 2003/0067393 A1* | 4/2003 | Albro et al. ................. 340/632 |

FOREIGN PATENT DOCUMENTS

| DE | 41 19 453 | 12/1992 |
| EP | 0 459 677 A2 | 12/1991 |
| EP | 1 004 871 A2 | 5/2000 |
| EP | 1 004 871 A3 | 4/2002 |
| JP | 06213784 | 5/1994 |
| WO | WO 02/40964 | 5/2002 |

OTHER PUBLICATIONS

PCT International Search Report for International Application No. PCT/GB03/05242 dated Mar. 10, 2004 (2 p.).

* cited by examiner

*Primary Examiner*—Hezron Williams
*Assistant Examiner*—John Fitzgerald
(74) *Attorney, Agent, or Firm*—Tod T. Tumey

(57) ABSTRACT

An analytical apparatus for automatically carrying out a plurality of analytical steps, which apparatus includes: a releasing device for releasing a sample from a sampling tube; device for analyzing a first portion of the released sample; a collecting device for collecting a second portion of the released sample; a device for re-released the collected said second portion of the sample; and a device for analyzing the re-released portion of the sample.

11 Claims, 2 Drawing Sheets

AUTOMATIC THERMAL DESORPTION APPARATUS AND METHOD

The present invention relates to an analytical apparatus and, more particularly, to an automatic thermal desorption apparatus, and a method for carrying out an automated analytical procedure.

It is known to provide a thermal desorption apparatus comprising an autosampler for automatically selecting one of a plurality of sampling tubes stored therein, heating the tube to desorb a sample from a sorbent material contained in the tube and then providing a flow of inert gas through the tube to drive the sample therefrom.

Known apparatus further comprise means for analysing a first portion of the sample driven from each sampling tube and for collecting a second portion of the sample in a respective collecting tube, for subsequent analysis.

However, a drawback of such known apparatus is that, following the analysis of samples released from a number of sampling tubes, their respective collecting tubes must be manually loaded into the autosampler for a subsequent analysis to be carried out.

A further drawback of such known apparatus is that automatic storage means must be provided for storing the collecting tubes in which respective portions of the samples released from each of the sampling tubes are collected, independent of the autosampler in which the sampling tubes are stored.

We have now devised an arrangement which overcomes the limitations of known analytical apparatus.

In accordance with the present invention, there is provided an analytical apparatus for automatically carrying out analytical steps, which apparatus comprises:
device for releasing a sample from a sampling tube;
device for analysing a first portion of the released sample;
device for collecting a second portion of the released sample; device for re-releasing the collected said second portion of the sample; and
device for analysing the re-released portion of the sample.

The apparatus may be arranged to select the sampling tube from a plurality of tubes stored in an autosampler. The apparatus thus obviates the requirement for the manual loading of collecting tubes into an autosampler, for a two stage analysis to be carried out on samples contained in a plurality of sampling tubes.

Preferably the apparatus is arranged to provide a comparison of the results from each of the two analysis stages.

Preferably, the second portion of the sample released from each sampling tube is collected either in the sampling tube itself or in a separate collecting tube or trap.

In the latter case, preferably either a single collecting tube or trap is used to collect, in turn, the second portion of the sample released from each of a plurality of sampling tubes, or respective collecting tubes are used to collect the second portion of each of the released samples, each of said respective collecting tubes preferably being selected automatically from a plurality of tubes stored either in the same autosampler as the sampling tubes or in a further autosampler.

Preferably, only a portion of the re-released sample is analysed, a second portion of the re-released sample being re-collected, either in the sampling tube or in a further respective re-collecting tube, each of said respective re-collecting tubes preferably being selected automatically from a plurality of tubes stored either in the same autosampler as the sampling tubes and/or collecting tubes or in a further autosampler.

The apparatus may be arranged such that the sample released from the sampling tube is buffered, by collecting the sample in an intermediate tube or trap, prior to the steps of analysing the first portion of the released sample and collecting the second portion of the released sample. Alternatively, the second portion of the sample released from the sampling tube, or subsequently collected and re-released, may be buffered, by collecting the sample in an intermediate tube or trap, prior to its collection/re-collection.

Also in accordance with the present invention, there is provided an analytical apparatus, comprising means for automatically carrying out, for each of a plurality of sampling tubes stored in an autosampler, the steps of:
selecting a sampling tube from said plurality of tubes;
releasing a sample from the sampling tube;
analysing a first portion of the released sample;
collecting a second portion of the released sample, either in the sampling tube or in a collecting tube selected from said plurality of tubes, with which said first tube is replaced in the autosampler.

The apparatus thus obviates the requirement for automatic storage means for storing the collecting tubes in which respective portions of the samples released from each of the sampling tubes are collected, independent of the autosampler in which the sampling tubes are stored.

The apparatus may also comprise means for automatically carrying out the further steps of releasing the sample collected in either the sampling tube or the collecting tube and analysing the released sample.

The apparatus may be arranged to analyse only a first portion of the sample released by said collecting means, a second portion of the released sample being re-collected, either in the sampling tube, the collecting tube or in a re-collecting tube selected from said plurality of tubes, with which either the sampling tube or the collecting tube is replaced in the autosampler.

The apparatus may be arranged such that, for each of the plurality of sampling tubes, the sample released from the sampling tube is buffered, by collecting the sample in a tube or trap, prior to the steps of analysing the first portion of the released sample and collecting the second portion of the released sample. Alternatively, the second portion of the sample released from the sampling tube or by the collecting means may be buffered, by collecting the sample in a tube or trap, prior to its collection/re-collection.

According to a further aspect of the present invention, there is provided an analytical method, which method includes:
releasing a sample from a sample tube;
analysing a first portion of the released sample;
collecting a second portion of the released sample;
re-releasing the collected second portion of the sample; and
analysing the re-released portion of the sample.

The sampling tube is typically selected from a plurality of tubes stored in an autosampler.

Preferably, the second portion of the sample released from each sampling tube is collected either in the sampling tube, or in a separate collecting tube or trap.

Preferably, only a portion of the re-released sample is analysed, a second portion of the re-released sample being re-collected, either in the sampling tube or in a further respective re-collecting tube, each of said respective re-collecting tubes stored either in the same autosampler as the sampling tubes and/or collecting tubes, or in a further autosampler.

It is preferred that the sample released from the sampling tube is buffered, typically by collecting the sample in an intermediate tube or trap, prior to the steps of analysing the first portion of the released sample and collecting the second portion of the released sample.

Alternatively, the second portion of the sample released from the sampling tube, or subsequently collected and re-released, may be buffered, typically by collecting the sample in an intermediate tube or trap, prior to its collection/recollection.

It is particularly preferred that the method is carried out using the analytical apparatus substantially as described hereinbefore.

Embodiments of the present invention will now be described by way of examples only and with reference to the accompanying drawings, of which:

Figure 1:
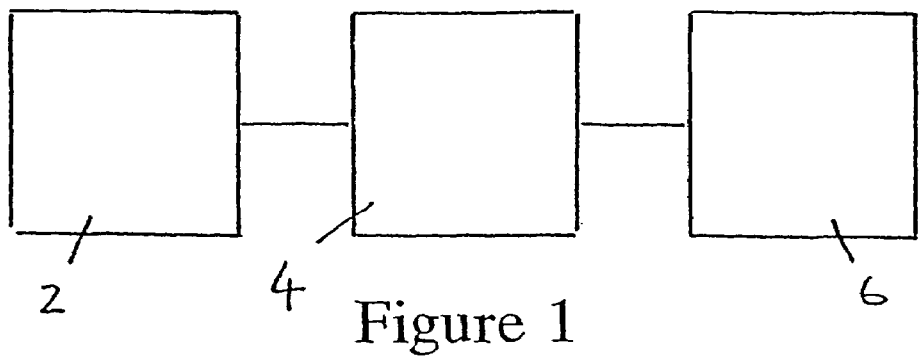
FIG. 1 is a schematic illustration of an embodiment of apparatus in accordance with the present invention.

Referring to FIG. 1, a first embodiment of analytical apparatus in accordance with the present invention is schematically illustrated, the apparatus comprising an autosampler 2, within which a plurality of sorbent tubes are stored (sampling tubes), analysis means 4 and a further sorbent tube (collecting tube) or trap 6. The autosampler may instead be replaced by a single sampling tube.

Figure 2:
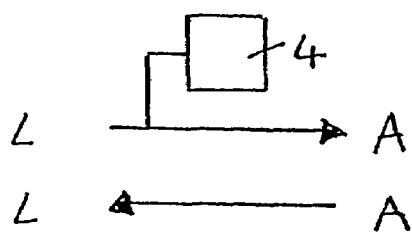
FIG. 2 to 5 are schematic illustrations of respective modes of operation of the apparatus of FIG. 1
Figure 3:
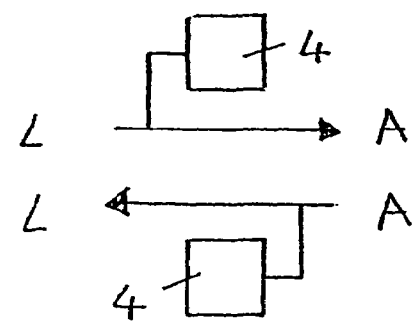

In a first mode of operation of the apparatus, illustrated in FIGS. 2 and 3, sampling tubes are automatically selected, in turn, from those stored in the autosampler. Each tube (L) is first heated to desorb a sample from a sorbent material contained therein and the desorbed sample driven from the tube by a flow of inert gas therethrough.

A first portion of the sample driven from the sampling tube (L) is analysed by the analysing means 4 and a second portion passed through the collecting tube (A), within which it is adsorbed by the sorbent material therein or contained in a trap.

The collecting tube (A) is then heated to desorb the sample from the sorbent material therein and is driven out of the tube by a reversed flow of inert gas.

The entire sample thus released from the collecting tube (A) may then be passed through the sampling tube (L), within which it is re-adsorbed for archiving or subsequent analysis (FIG. 2), or only a portion of the sample may be passed through the sampling tube (L) for re-adsorption, with a second portion of the sample being analysed by the analysing means 4 (FIG. 3). In the former case the apparatus preferably comprises means for cooling the sampling tube (L) to facilitate re-adsorption by the sorbent material contained therein. In both cases, the apparatus preferably comprises means for cooling the collecting tube (A) to facilitate adsorption by the sorbent material contained therein.

Figure 4:
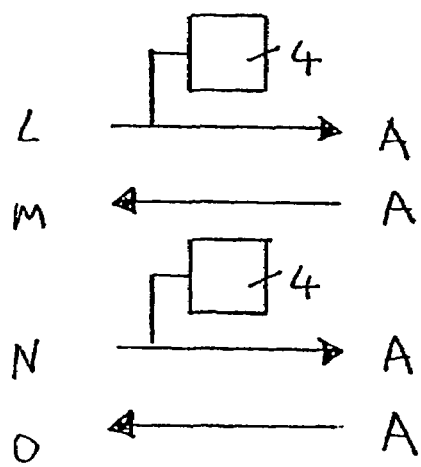
Figure 5:
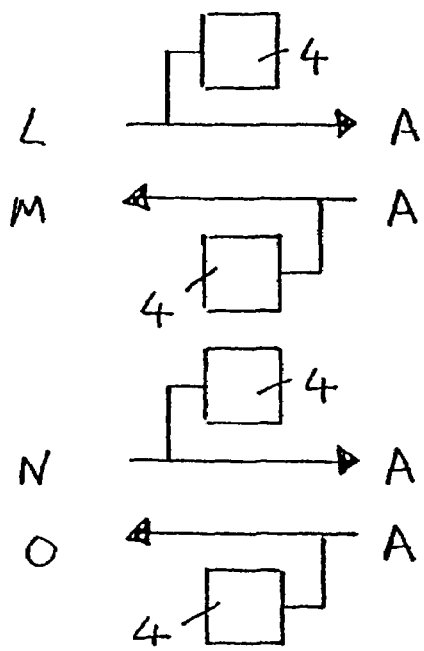

In a first modification of the above process, illustrated schematically in FIGS. 4 and 5, the whole (FIG. 4) or a portion (FIG. 5) of the sample released from the collecting (A) tube may be passed though a sorbent tube (M) other than the sampling tube (re-collecting tube), with which the sampling tube (L) is replaced in the autosampler.

Figure 6:
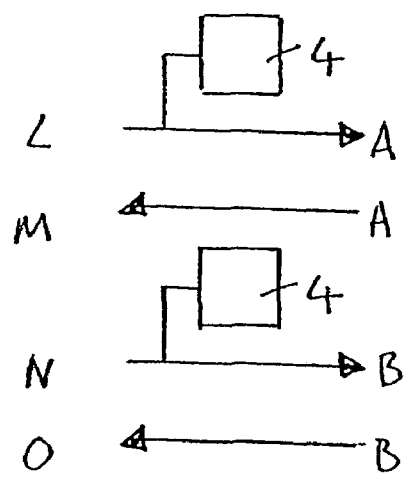
FIG. 6 and 7 are schematic illustrations of respective modes of operation of a second embodiment of apparatus in accordance with the present invention.
Figure 7:
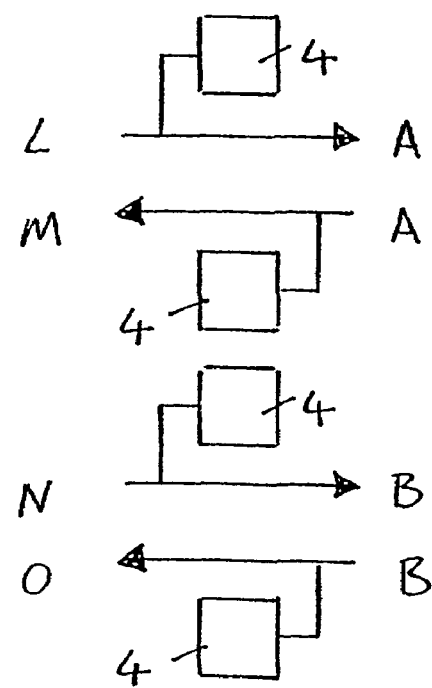

The same process may be repeated for each sampling tube (L,N) selected from the autosampler, either using a single collecting tube (A) for collecting the second portion of the sample released from each sampling tube (FIGS. 4 and 5) or using a respective collecting tube (A,B) for each sample, as illustrated schematically in FIGS. 6 and 7, with each collecting tube being selected, in turn, from a plurality of collecting tubes stored in a second autosampler. In the former case, the apparatus preferably comprises means for cooling the collecting tube (A) to facilitate adsorption by the sorbent material contained therein.

As a variation on the processes illustrated in FIGS. 2, 4, and 6, the entire sample driven from each sampling tube may be collected in a collecting tube, a first portion of the sample subsequently released from the collecting tube being analysed by the analysing means 4, with a second portion of the sample being re-collected in the sampling tube or a re-collection tube. The apparatus preferably comprises means for cooling the collecting tube to facilitate adsorption by the sorbent material contained therein.

It would also remain in accordance with the present invention, in those embodiments in respect of which the use of only a single collecting tube has been described, for the collecting tube to be substituted with a trap.

The various apparatus thus described provide an efficient and labour saving means for the thermal desorption of a plurality of samples contained in respective sampling tubes, wherein a portion of the desorbed sample is to be collected for subsequent analysis.

The invention claimed is:

1. An analytical apparatus arranged to carry out automatically a plurality of analytical steps during thermal desorption of a sample, which apparatus includes:
   a releasing device for releasing a sample from a sampling tube to provide a released sample;
   analyser for analysing a first portion of the released sample;
   a re-collection device for collecting a second portion of the released sample;
   a re-release device for re-releasing the collected said second portion of the released sample that has been collected to provide a re-released portion of the sample for archiving or further analysis, wherein the second portion of the sample released is re-collected in one of the following re-collection devices: a) either in the sampling tube or b) a single collecting tube or trap which is used to collect, in turn, the second portion of the sample released from each of a plurality of sampling tubes or c) respective collecting tubes are used to collect the second portion of each of the released samples, with each of said respective collecting tubes being selected automatically from a plurality of tubes stored either in the same autosampler as the sampling tubes or in a further autosampler.

2. The analytical apparatus according to claim 1, which is arranged to select the sampling tube from a plurality of tubes stored in an autosampler.

3. The analytical apparatus according to claim 1, which is arranged to provide a comparison of the results from each of the two analysis stages.

4. The analytical apparatus according to claim 1, wherein a portion of the re-released sample is analysed, a second portion of the re-released sample being re-collected, either in the sampling tube or in a further respective re-collecting tube, each of said respective re-collecting tubes being selected automatically from a plurality of tubes stored either in the same autosampler as the sampling tubes, collecting tubes, or both or in a further autosampler.

5. The analytical apparatus according to claim 1, arranged such that the sample released from the sampling tube is buffered, by collecting the sample in an intermediate tube or trap, prior to the steps of analysing the first portion of the released sample and collecting the second portion of the released sample.

6. The analytical apparatus according to claim 1, wherein the second portion of the sample released from the sampling tube, or subsequently collected and re-released, are buffered, by collecting the sample in an intermediate tube or trap, prior to its collection and re-collection.

7. An analytical apparatus comprising means arranged to carry out automatically a plurality of analytical steps during thermal desorption of a sample for each of a plurality of sampling tubes stored in an autosampler, the apparatus comprising:
- a tube selector for selecting a first sampling tube from said plurality of tubes;
- a release device for releasing a sample from the first sampling tube to provide a released sample;
- an analyser for analysing a first portion of the released sample; and
- a re-collection device for collecting a second portion of the released sample, either in a) each respective first sampling tube or in b) a collecting tube selected automatically from said plurality of sampling tubes, with which the first sampling tube is replaced by the collecting tube within the autosampler.

8. An apparatus according to claim 7, which further comprises means for automatically carrying out the further steps of releasing the sample collected in either the sampling tube or the collecting tube and analysing the released sample.

9. An apparatus according to claim 7, which is arranged to analyse only a first portion of the sample released by said re-collection device, a second portion of the released sample being re-collected, either in the sampling tube, the collecting tube or in a re-collecting tube selected from said plurality of tubes, with which either the sampling tube or the collecting tube is replaced in the autosampler.

10. An apparatus according to claim 7, wherein for each of the plurality of sampling tubes, the sample released from the sampling tube is buffered, by collecting the sample in a tube or trap, prior to the steps of analysing the first portion of the released sample and collecting the second portion of the released sample.

11. An apparatus according to claim 7, wherein the second portion of the sample released from the sampling tube or by the collecting means may be buffered, by collecting the sample in a tube or trap, prior to its collection/re-collection.

* * * * *